United States Patent
Schrier et al.

[11] Patent Number: 6,069,014
[45] Date of Patent: *May 30, 2000

[54] DEVICES AND METHODS FOR SEPARATING CELLULAR COMPONENTS OF BLOOD FROM LIQUID PORTION OF BLOOD

[75] Inventors: Wayne H. Schrier, Half Moon Bay; Corey L. Jaseph, Mountain View; Ronald J. Schoengold, San Jose, all of Calif.; Franco Ruggeri, Milan, Italy

[73] Assignee: Beckman Coulter, Inc., Fullerton, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/914,426

[22] Filed: Aug. 19, 1997

Related U.S. Application Data

[62] Division of application No. 08/437,850, May 9, 1995, abandoned.

[51] Int. Cl.⁷ .................. C01N 33/543; C01N 33/558
[52] U.S. Cl. .............. 436/518; 422/56; 422/58; 422/101; 435/2; 435/4; 435/7.1; 435/7.92; 435/287.1; 435/287.2; 435/287.7; 435/287.8; 435/287.9; 435/805; 435/810; 435/970; 436/514; 436/169; 436/170; 436/177; 436/178; 436/808; 436/810
[58] Field of Search ................. 422/56, 58, 101; 435/2, 4, 7.1, 7.92, 287.1, 287.2, 287.7, 287.8, 287.9, 805, 810, 962, 97; 436/514, 518, 169, 170, 177, 178, 808, 810

[56] References Cited

U.S. PATENT DOCUMENTS

| | | |
|---|---|---|
| 3,723,064 | 3/1973 | Liotta . |
| 3,768,978 | 10/1973 | Grubb et al. . |
| 3,902,964 | 9/1975 | Greenspan . |
| 3,990,850 | 11/1976 | Friedman et al. . |
| 4,066,403 | 1/1978 | Bruschi . |
| 4,110,079 | 8/1978 | Schaeffer et al. . |
| 4,160,008 | 7/1979 | Fenocketti et al. . |
| 4,248,829 | 2/1981 | Kitajima et al. . |
| 4,255,384 | 3/1981 | Kitajima et al. . |
| 4,256,693 | 3/1981 | Kondo et al. . |
| 4,271,119 | 6/1981 | Columbus . |
| 4,288,228 | 9/1981 | Oberhardt . |
| 4,426,451 | 1/1984 | Columbus . |
| 4,477,575 | 10/1984 | Vogel et al. . |
| 4,594,327 | 6/1986 | Zuk . |
| 4,678,757 | 7/1987 | Rapkin et al. . |
| 4,753,776 | 6/1988 | Hillman et al. . |
| 4,780,280 | 10/1988 | Berger et al. . |
| 4,790,979 | 12/1988 | Terminiello et al. . |

(List continued on next page.)

OTHER PUBLICATIONS

Liu et al., "AccuMeter® Noninstrumented Quantitative Assay of High–Density Lipoprotein in Whole Blood," *Clinical Chemistry*, vol. 39 No. 9, pp. 1948–1952 (1993).

*Primary Examiner*—Christopher L. Chin
*Attorney, Agent, or Firm*—William H. May; Margaret A. Kivinski

[57] ABSTRACT

A device for the separation of the liquid portion of blood from the cellular components of blood comprises: (1) a pad of porous material permeable to the liquid portion of blood but capable of trapping the cellular components of blood; (2) a substrate supporting the pad; and (3) means, attached to the pad, for facilitating the flow of the liquid portion of the blood: (i) through interstices around the trapped cellular components of the blood and (ii) from the pad of porous material. The separation of the liquid portion of blood from the cellular components of the blood occurs by flow through the pad of porous material without significant hemolysis. The device can be incorporated into a device for the performance of specific binding assays such as immunoassays. The pad of porous material can contain an agglutinating agent such as a lectin or an anti-blood cell antibody, or a carbohydrate such as mannitol. Other devices and methods for the separation of the liquid portion of blood from the cellular components of the blood are also disclosed.

35 Claims, 3 Drawing Sheets

U.S. PATENT DOCUMENTS

| | | |
|---|---|---|
| 4,816,224 | 3/1989 | Vogel et al. . |
| 4,876,067 | 10/1989 | Deneke et al. . |
| 4,883,764 | 11/1989 | Kloepfer . |
| 4,933,092 | 6/1990 | Aunet et al. . |
| 4,943,522 | 7/1990 | Eisinger et al. . |
| 4,963,325 | 10/1990 | Lennon et al. . |
| 5,055,195 | 10/1991 | Trasch et al. . |
| 5,064,541 | 11/1991 | Jeng et al. . |
| 5,076,925 | 12/1991 | Roesink et al. . |
| 5,096,809 | 3/1992 | Chen et al. . |
| 5,104,811 | 4/1992 | Berger et al. . |
| 5,118,428 | 6/1992 | Sand et al. . |
| 5,118,472 | 6/1992 | Tanaka et al. . |
| 5,130,258 | 7/1992 | Makino et al. . |
| 5,132,208 | 7/1992 | Freitag et al. . |
| 5,135,719 | 8/1992 | Hillman et al. . |
| 5,209,904 | 5/1993 | Forney et al. . |
| 5,212,060 | 5/1993 | Maddox . |
| 5,215,886 | 6/1993 | Patel et al. . |
| 5,240,862 | 8/1993 | Koenhen et al. . |
| 5,262,067 | 11/1993 | Wilk et al. . |
| 5,306,623 | 4/1994 | Kiser et al. . |
| 5,364,533 | 11/1994 | Ogura et al. . |
| 5,397,479 | 3/1995 | Kass et al. . |
| 5,652,148 | 7/1997 | Deshi et al. ............................ 436/178 |

DEVICES AND METHODS FOR SEPARATING CELLULAR COMPONENTS OF BLOOD FROM LIQUID PORTION OF BLOOD

CROSS-REFERENCE TO RELATED APPLICATIONS

This is a Divisional of application Ser. No. 08/437,850, filed May 9, 1995, now abandoned, which application(s) are incorporated herein by reference.

This application is related to copending U.S. patent application Ser. No. 08/040,430 by Howard M. Chandler et al., entitled "Opposable-Element Chromatographic Assay Device," and filed Mar. 31, 1993 now U.S. Pat. No. 5,877,028, and to copending U.S. patent application Ser. No. 08/119,466, now U.S. Pat. No. 5,441,698 by Joyce L. Norell, entitled "Bevel Closure and Device," and filed Sep. 10, 1993. The disclosures of these applications are incorporated herein by this reference.

BACKGROUND OF THE INVENTION

This invention is directed to methods and devices for separating cellular elements of blood from the liquid portion of blood, particularly in connection with the determination of characteristics of blood samples.

Among the many analytical systems used for detection and/or determination of analytes, particularly analytes of biological interest, are chromatographic assay systems. Among the analytes frequently assayed with such systems are:

(1) hormones, such as human chorionic gonadotropin (hCG), frequently assayed as a marker of human pregnancy;

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibody to the bacteria *Helicobacter pylori* and to human immunodeficiency virus (HIV);

(4) other proteins, including tumor markers such as carcinoembryonic antigen and α-fetoprotein;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers, and anticonvulsants, and illegal drugs of abuse, such as cocaine, heroin, and marijuana;

(7) environmental pollutants such as pesticides and aromatic hydrocarbons; and (8) vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such systems are the "thin layer" system in which a solvent moves across a thin, flat absorbent medium. Among the most important of tests that can be performed with such thin layer systems are immunoassays, which depend on the specific interaction between an antigen or hapten and the corresponding antibody to form antigen-antibody complexes. The antigen to be detected can itself be an antibody, such as in serological assays for *H. pylori*-specific antibody. In such cases, the antibody to be detected can also be bound to a specific antigen. Alternatively, the antigen to be detected can be detected indirectly by using a labeled second antibody that binds to the first antibody to the analyte to be detected. These immunoassays as a means for testing for the presence and/or amount of clinically important molecules have been known for some time. As early as 1956, J. M. Singer reported the use of an immune-based latex agglutination test for detecting a factor associated with rheumatoid arthritis (Singer et al., *Am. J. Med.* 22:888–892 (1956)).

Immunoassays generally use a disclosing reagent or particle that has been linked to an antibody, i.e., a labeled reagent or component, to the molecule to be assayed, forming a conjugate. This conjugate is then mixed with a specimen, and if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, or another physical or chemical property. The specific reactions that are employed vary with the nature of the molecule being assayed and the sample to be tested. Immunoassays have been used with chromatographic methods and devices; this combination is known as immunochromatography.

Immunochromatographic assays fall into two principal categories: "sandwich" and "competitive," according to the nature of the antigen-antibody complex to be detected and the sequence of reactions required to produce that complex.

In general, the sandwich immunochromatographic procedures call for mixing the sample that may contain the analyte to be assayed with antibodies to the analyte. These antibodies are mobile and typically are linked to a label or a disclosing reagent, such as dyed latex, a colloidal metal sol, or a radioisotope. This mixture is then applied to a chromatographic medium containing a band or a zone of immobilized antibodies to the analyte of interest. The chromatographic medium is often in the form of a strip resembling a dipstick. When the complex of the molecule to be assayed and the labeled antibody reaches the zone of the immobilized antibodies on the chromatographic medium, binding occurs and the bound labeled antibodies are localized at the zone. This indicates the presence of the molecule to be assayed. This technique can be used to obtain quantitative or semi-quantitative results.

In other variations of this technique, if an antibody is to be detected, the immobilized material on the dipstick can be a corresponding antigen, and the labeled antibody can be a second antibody that binds the first antibody on the basis of a specificity such as species or class specificity. For example, if a human antibody to a particular bacterial antigen is to be detected, the bacterial antigen can be immobilized on the dipstick and the antibody can be detected with labeled goat anti-human antibody.

Examples of sandwich immunoassays performed on test strips are described by U.S. Pat. No. 4,168,146 to Grubb et al. and U.S. Pat. No. 4,366,241 to Tom et al., both of which are incorporated herein by this reference.

In competitive immunoassays, the disclosing reagent is typically coupled to an analyte or analyte analog which competes for binding with an antibody with any unlabeled analyte present in this sample. Competitive immunoassays are typically used for detection of analytes such as haptens, each hapten being monovalent and capable of binding only one antibody molecule. Examples of haptens include therapeutic drugs such as theophylline and digoxin and drugs of abuse such as cocaine and heroin and their metabolites. Examples of competitive immunoassay devices are those disclosed by U.S. Pat. No. 4,235,601 to Deutsch et al., U.S. Pat. No. 4,442,204 to Liotta, and U.S. Pat. No. 5,208,535 to Buechler et al., all of which are incorporated herein by this reference.

One of the samples most frequently assayed for an analyte using test strips or similar devices is blood. Most typically, the analyte to be assayed is a soluble component in the liquid portion of blood, i.e., serum or plasma. The compositions of the two are similar, except that serum, obtained from a blood sample that has been allowed to clot, is lacking in fibrinogen and certain other clotting factors that are depleted as a result of the clotting process.

Most typically, the clinician or technician will draw a blood sample, which is often a fairly small sample. It would be preferable to be able to use the entire blood sample for the assay, avoiding the necessity of a bulk preparation of serum or plasma from the blood sample. However, with most test strips and similar analytical devices, the use of whole blood as a sample, or even a blood sample from which the cells, particularly the erythrocytes, have been partially removed, is undesirable.

The blood cells, particularly the erythrocytes, first slow the flow of serum or plasma along the membrane and ultimately stop it by clogging the pores of the membrane. This results in an invalid test. The migration of red blood cells or other blood cells can also create high backgrounds or otherwise interfere with the performance of the test carried out by the assay device. Although blood cells can be removed by filtration through microporous filters, the action of such filters is generally too slow to permit efficient assay of cell-free blood.

Additionally, even if the blood cells are effectively removed, methods for doing so frequently result in hemolysis. The occurrence of hemolysis is undesirable because it results in the release of enzymes, hemoglobin, other pigments, and stromata into the cell-free portion of blood. This causes interference with many clinical tests.

Various methods for the separation of blood cells from the liquid portion of blood are described, for example in U.S. Pat. No. 3,768,978 to Grubb et al., U.S. Pat. No. 3,902,964 to Greenspan, U.S. Pat. No. 4,477,575 to Vogel et al., U.S. Pat. No. 4,594,372 to Zuk, U.S. Pat. No. 4,753,776 to Hillman et al., U.S. Pat. No. 4,816,224 to Vogel et al., U.S. Pat. No. 4,933,092 to Aunet et al., U.S. Pat. No. 5,055,195 to Trasch et al., U.S. Pat. No. 5,064,541 to Jeng et al., U.S. Pat. No. 5,076,925 to Roesink et al., U.S. Pat. No. 5,118,428 to Sand et al., U.S. Pat. No. 5,118,472 to Tanaka et al., U.S. Pat. No. 5,130,258 to Makino et al., U.S. Pat. No. 5,135,719 to Hillman et al., U.S. Pat. No. 5,209,904 to Forney et al., U.S. Pat. No. 5,212,060 to Maddox et al., U.S. Pat. No. 5,240,862 to Koenhen et al., U.S. Pat. No. 5,262,067 to Wilk et al., U.S. Pat. No. 5,306,623 to Kiser et al., U.S. Pat. No. 5,364,533 to Ogura et al., and U.S. Pat. No. 5,397,479 to Kass et al., all of which are incorporated herein by this reference.

However, there is still a need for an improved method of separation of the cellular components of blood from the liquid portion of blood for rapid and accurate assay of analytes contained in the liquid portion of blood. Particularly, there is a need for an integrated device that incorporates both an assay element and means for separating the liquid portions of blood from the cellular components of blood so that an analyte present in the liquid portions of blood can be assayed readily in a single device. Such an improved device would avoid the necessity of a preliminary extraction of serum or plasma with its attendant necessity of safe disposal of the blood fractions. This has become a serious problem due to the increased spread of blood-borne diseases such as hepatitis and AIDS. An improved device would be capable of direct assay of the desired analyte when a whole blood sample is applied to the device.

Preferably, such a device should be able to perform a broad range of immunoassays, including both sandwich and competitive immunoassays.

SUMMARY

We have developed devices and methods for separating the liquid portions of whole blood from the cellular components of blood, as well as assay devices and methods for their use, that meet these needs.

One aspect of the device is a device for separating the liquid portion of blood from the cellular components of blood comprising:

(1) a pad of porous material permeable to the liquid portion of blood but capable of trapping the cellular components of blood;

(2) a substrate supporting the pad; and (3) means, attached to the pad, for facilitating the flow of the liquid portion of the blood: (i) through interstices around the trapped cellular components of the blood within the pad and (ii) from the pad of porous material.

The separation of the liquid portion of blood from the cellular components of the blood occurs by flow through the pad without significant hemolysis.

Typically, the pad of porous material contains a binder for the cellular components of blood. If the binder is an anti-blood cell antibody, it is preferably an anti-erythrocyte antibody. If the binder is a lectin, a number of types of lectins are suitable for use.

Alternatively, the pad can be impregnated with a carbohydrate capable of aggregating blood cells. A number of carbohydrates are suitable for use. Preferably, the carbohydrate is mannitol.

The pad of porous material in this device can include two sectors: (i) a first sector permeable to both the liquid portion of blood and the cellular components of blood; and (ii) a second sector permeable to the liquid portion of blood but capable of binding the cellular components of blood.

Alternatively, the pad of porous material permeable to the liquid portion of blood but capable of trapping the cellular components of blood can include therein an asymmetric membrane with a first surface and a second surface, the membrane having a gradient of pore sizes such that the pore size decreases from the first surface to the second surface, the asymmetric membrane capable of trapping the cellular components of blood within it and allowing the liquid components of blood to pass through.

The means, attached to the pad, for facilitating the flow of the liquid portion of the blood typically includes therein a membrane for chromatographic separation; the membrane for chromatographic separation typically has a capture zone thereon for binding a member of a specific binding pair.

This device, and other analogous devices described below, can be used in a method of separating the liquid portion of blood from the cellular components of blood. If a membrane for chromatographic separation is included, the device can be used in a method for performing an assay for detecting and/or determining at least one analyte in the liquid portion of a blood sample.

One aspect of the present invention is a device for separating the liquid portion of blood from the cellular components of blood comprising:

(1) a first porous separating matrix permeable to the liquid portion of blood but capable of trapping the cellular components of blood; and (2) a second porous matrix in operable contact with the first porous separating matrix that permits the liquid portion of the blood to flow by capillary action or chromatographic separation through the second porous matrix.

The separation of the liquid portion of blood from the cellular components of the blood occurs by flow through the first and second matrices without significant hemolysis.

In this version of the device according to the present invention, the second matrix is typically a membrane for chromatographic separation, thus producing an assay device. The membrane for chromatographic separation typically has a capture zone thereon for binding a member of a specific binding pair.

If the second matrix is a membrane for chromatographic separation, a method for performing an assay for detecting and/or determining at least one analyte in the liquid portion of a blood sample can comprise the steps of:

(1) applying a sample of blood to the first porous separating matrix of the device;

(2) allowing the blood sample to flow through the first porous separating matrix to separate the liquid portion of the blood sample from the cellular components of the blood sample;

(3) facilitating the flow of the liquid portion of the blood through the interstices around the trapped cellular components of the blood as a result of the action of the second matrix; and (4) allowing the liquid portion of the blood to flow through the second matrix so that an assay is performed in the second matrix, the assay being performed by binding a member of a specific binding pair to the capture zone of the second matrix to detect and/or determine the at least one analyte.

The first separating matrix can be an asymmetric membrane with a first surface and a second surface. The membrane has a gradient of pore sizes such that the pore size decreases from the first surface to the second surface; the asymmetric membrane is capable of trapping the cellular components of blood within it and allowing the liquid components of blood to pass through.

Typically, the device further comprises an impermeable solid support to which the second matrix is fixedly attached.

Yet another aspect of the invention is a device for the separation of the liquid portion of blood from the cellular components of blood comprising three matrices. Such a device can comprise:

(1) a first porous separating matrix permeable to the liquid portion of blood but capable of trapping the cellular components of blood;

(2) a second porous separating matrix in operable contact with the first porous separating matrix permeable to the liquid portion of blood but capable of trapping the cellular components of blood; and (3) a third porous matrix in operable contact with the second porous separating matrix that permits the liquid portion of the blood to flow by capillary action or chromatographic separation through the second porous matrix.

The separation of the liquid portion of the blood from the cellular components of the blood occurs by flow through the first and second porous separating matrices without significant hemolysis.

Yet another embodiment of a device according to the present invention has multiple second porous matrices. Such a device comprises:

(1) a first porous separating matrix permeable to the liquid portion of blood but capable of trapping the cellular components of blood; and (2) at least two second porous matrices, each second porous matrix in operable contact with the first porous separating matrix that permits the liquid portion of the blood to flow by capillary action or chromatographic separation through the second porous matrix.

Still another aspect of the present invention is a two-component device for separating the liquid portion of a blood sample from the cellular components. This device comprises:

(1) a first opposable component including:
 (a) a first porous separating matrix permeable to the liquid portion of blood but capable of trapping the cellular components of blood; and
 (b) a second porous matrix in operable contact with the first porous separating matrix that permits the liquid portion of the blood to flow by capillary action or chromatographic separation through the second porous matrix; and (2) a second opposable component attachable to the first opposable component such that the first and second opposable components can be brought into opposition to transfer fluid from one of the opposable components to the other by pressure.

The separation of the liquid portion of blood from the cellular components of the blood occurs by flow through the first and second matrices of the first opposable component without significant hemolysis.

The second opposable component can include a sample preparation zone, which can include at least one reagent for treatment of the sample or a specific binding partner labeled with a detectable label, the specific binding partner having specific binding affinity for at least one component selected from the analyte and a specific binding partner for the analyte in a form that can be resolubilized by the addition of an aqueous sample to the sample preparation zone.

A two-component device particularly adapted to bidirectional assays can comprise:

(1) a first opposable component including:
 (a) a first porous separating matrix permeable to the liquid portion of blood but capable of trapping the cellular components of blood; and
 (b) a second porous matrix including a membrane for chromatographic separation in operable contact with the first porous separating matrix that permits the liquid portion of the blood to flow in a first direction by capillary action or chromatographic separation through the second porous matrix; and (2) a second opposable component attachable to the first opposable component such that the first and second opposable components can be brought into opposition to transfer a reagent from the second opposable component to the first opposable component by pressure such that bringing the first and second opposable components into opposition causes the reagent transferred from the second opposable component to the first opposable component to migrate through the second porous matrix in a second direction opposite to the first direction.

In this version, the separation of the liquid portion of blood from the cellular components of the blood occurs by flow through the first and second matrices of the first opposable component without significant hemolysis.

Another aspect of the present invention is a method for separating the liquid portion of blood from the cellular components of blood comprising the steps of:

(1) adding a cross-linking substance for the cellular components of blood to a sample of whole blood, the cross-linking substance being selected from the group consisting of a lectin, an anti-blood cell antibody, and a carbohydrate capable of aggregating blood cells;

(2) mixing the cross-linking substance and the blood sample to form a mixture of the cross-linking substance and the blood sample;

(3) applying the mixture of the cross-linking substance and the blood sample to a device for separating the liquid portion of blood from the cellular components of blood, the device comprising:

(a) a pad of porous material permeable to the liquid portion of blood but capable of trapping the cellular components of blood aggregated by the reaction between the cross-linking substance and the blood sample;

(b) a substrate supporting the pad; and (c) means, attached to the pad, for facilitating the flow of the liquid portion of the blood: (i) through interstices around the trapped cellular components of the blood and (ii) from the pad of porous material, whereby the separation of the liquid portion of blood from the cellular components of the blood occurs by flow through the pad without significant hemolysis; and (d) allowing the liquid portion of the blood to flow through the pad to separate the liquid portion of the blood from the cellular components of the blood.

Preferably, the method further comprises adding an anticoagulant together with the cross-linking substance. Typically, the anticoagulant is heparin or EDTA.

Preferably, a concentration of cross-linking substance is used that is sufficient to cross-link substantially all cellular elements of blood.

An alternative method for separating the liquid portion of blood from the cellular components of blood comprises the steps of:

(1) adding a sample of blood to a capillary tube coated with a cross-linking substance as described above;

(2) allowing and cross-linking substance to dissolve in the blood sample to form a mixture of the cross-linking substance and the blood sample;

(3) applying the mixture of the cross-linking substance and the blood sample to a device for separating the liquid portion of blood from the cellular components of blood as described above; and (4) allowing the liquid portion of the blood to flow through the pad to separate the liquid portion of the blood from the cellular components of the blood.

Preferably, the capillary tube is also coated with an anti-coagulant.

BRIEF DESCRIPTION OF THE DRAWINGS

These and other features, aspects, and advantages of the present invention will become better understood with reference to the following description, appended claims, and accompanying drawings where:

DESCRIPTION

Definitions

Figure 1:
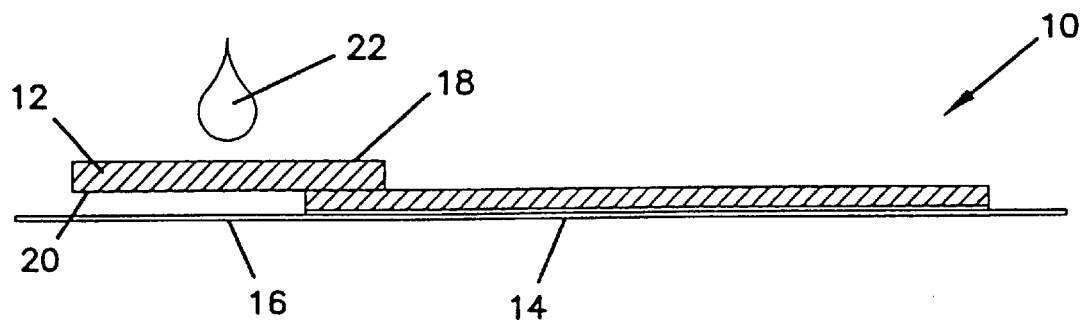
FIG. 1 is a drawing of a device for separating the liquid portion of blood from the cellular components of blood, employing a pad of porous material.

In the context of this disclosure, the following terms are defined as follows unless otherwise indicated:

Specific Binding Partner: A member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, substrate analog-enzyme, inhibitor-enzyme, carbohydrate-lectin, biotin-avidin, and virus-cellular receptor.

Operable Contact: Two solid components are in operable contact when they are in contact, either directly or indirectly, in such a manner that an aqueous liquid can flow from one of the two components to the other substantially uninterruptedly, by capillarity or otherwise "Direct contact" means that the two elements are in physical contact, such as edge-to-edge or front-to-back. Typically, when two components are in direct contact, they are overlapped with an overlap of about 0.5 mm to about 5 mm. However, the components can be placed with abutting edges. "Indirect contact" means that the two elements are not in physical contact, but are bridged by one or more conductors.

Analyte: The term "analyte" includes both the actual molecule to be assayed and analogs and derivatives thereof when such analogs and derivatives bind another molecule used in the assay in a manner substantially equivalent to that of the analyte itself.

Antibody: The term "antibody" includes both intact antibody molecules of the appropriate specificity and antibody fragments (including Fab, F(ab'), and F(ab')$_2$ fragments) as well as chemically modified intact antibody molecules and antibody fragments, including hybrid antibodies assembled by in vitro reassociation of subunits and single-chain antibody molecules produced by genetic engineering. Also included within the definition are anti-idiotypic antibodies that specifically bind antigen-combining sites of antibodies.

Without Significant Hemolysis: The term "without significant hemolysis" means the absence of hemolysis to a degree such that the resulting plasma or serum shows no apparent redness against a white background by visual inspection.

Supported: The term "supported" can include either directly or indirectly supported, as directly by a solid substrate or indirectly by a solid substrate through one or more intervening elements.

Cross-linking Substance: The term "cross-linking substance" is used generically herein to include substances that are capable of cross-linking, agglutinating, or aggregating the cellular components of blood. Specifically, this term includes lectins and anti-blood cell antibodies, as well as carbohydrates that can aggregate blood cells by making them adhesive and causing them to clump.

Methods and devices according to the present invention use one of two techniques for separating the cellular elements (formed elements) of blood from the liquid portion of blood (serum or plasma, containing the soluble elements), for use in an immunochromatographic test format.

The first of these techniques is active separation of the cellular elements of blood from the liquid portion of blood on or as an integral part of the test device, referred to generally as on-board processing. The second of these techniques is separation or blood sample processing before the sample is added to the test device, referred to generally as off-board processing.

I. DEVICES AND METHODS FOR ON-BOARD PROCESSING

A. General Description of On-Board Processing

One aspect of the present invention is devices for separating the liquid portion of blood from the cellular components of blood on or as an integral part of the test device. The cellular components of blood include erythrocytes (red blood cells), leukocytes (white blood cells) and platelets. The liquid portion of the blood includes the remainder of the blood and is generally known as serum if the blood has clotted, forming a clot containing fibrin and the blood cells. It is generally known as plasma if it is obtained from unclotted blood. The major ingredient present in plasma but absent in serum is fibrinogen, the precursor of fibrin.

In general, such a device comprises:

(1) a pad of porous material permeable to the liquid portion of blood but capable of trapping the cellular components of blood;

(2) a subs t rate supporting the pad; and (3) means, attached to the pad, for facilitating the flow of the liquid portion of the blood: (i) through interstices around the trapped cellular components of the blood and (ii) from the pad of porous material.

In general, a method for separating the liquid portion of blood from the cellular components of blood using this device comprises:

(a) applying a sample of blood to the pad of porous material of the device;

(b) allowing the blood sample to flow through the pad of porous material to separate the liquid portion of the blood sample from the cellular components of the blood sample; and (c) facilitating the flow of the liquid portion of the blood through the interstices around the trapped cellular components of the blood and from the pad of porous material.

Various arrangements and elaborations of this device are within the scope of the present invention, as described further below.

The separation of the liquid portion of blood from the cellular components of the blood occurs by flow through the pad without significant hemolysis.

Typically, the substrate is a solid, substantially planar substrate. Typically, the flow through the pad occurs in a direction substantially parallel to or along the substrate.

The means, attached to the pad, for facilitating the flow of the liquid portion of the blood can include therein a membrane for chromatographic separation; typically, the membrane has a capture zone thereon for binding a member of a specific binding pair. In this arrangement, the device can be used in a method for performing an assay for detecting and/or determining at least one analyte in the liquid portion of a blood sample comprising the steps of:

(1) applying a sample of blood to the pad of porous material of the device;

(2) allowing the blood sample to flow through the pad of porous material to separate the liquid portion of the blood sample from the cellular components of the blood sample;

(3) facilitating the flow of the liquid portion of the blood through the interstices around the trapped cellular components of the blood as a result of the action of the means attached to the pad; and (4) allowing the liquid portion of the blood to flow through the chromatographic medium so that an assay is performed in the chromatographic medium, the assay being performed by binding a member of a specific binding pair to the capture zone of the chromatographic medium to detect and/or determine the at least one analyte.

The conditions that are optimal for the performance of such assays, such as the choice of the member of the specific binding pair, the use of buffers or salts, the time required, and the optimum temperature, are well known in the art and need not be described further here.

The porous pad, also referred to as a sample pad because the sample is typically applied to it, can be a woven or non-woven fabric, paper, cellulose, glass fiber, polyester, other polymers, or mixtures of these materials to retain the cellular components of blood. The porous pad typically has a binder for the cellular components of blood incorporated therein.

The binder for the cellular components of blood is typically a lectin or an anti-blood cell antibody. When the binder is an anti-blood cell antibody, it is typically an anti-erythrocyte antibody. Such antibodies are well known in the art and need not be described further here. Typically, they are obtained by the injection of red blood cells or fractions from red blood cells into a different species. If the desired antibody is anti-human red blood cell antibody, suitable animals for the production of such antibodies include goats, rabbits, horses, and sheep. Either polyclonal or monoclonal antibodies can be used. Alternatively, anti-leukocyte or anti-platelet antibodies can be used alone or in addition to the anti-red blood cell antibody if it is desired to ensure removal of those cellular components.

The binder for the cellular components of blood can be noncovalently bound to the sample pad. Alternatively, it can be covalently cross-linked to the sample pad; techniques for cross-linking proteins to solid supports such as cellulose, paper, and other typical sample pad materials are well-known in the art and need not be described further here. The sample pad, containing antibodies or lectins, can be further treated with polyester binders to capture cellular elements, as described, for example, in U.S. Pat. No. 4,816,224 to Vogel et al., incorporated herein by reference. Other types of polymer binders can also be used.

When the binder is a lectin, typically the lectin is one of the following, but is not limited to: concanavalin A, abrin, phytohaemagglutinin, limulin, or one of the lectins produced by the following species: *Agaricus bisporus, Anguilla anguilla, Arachis hypogaea, Bandeiraea simplicifolia, Bauhinia purpurea, Caragana arborescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Lycopersicon esculentum, Maclura pomifera, Momordica charantia, Mycoplasma gallisepticum, Naja mocambique, Naja kaouthia, Perseau americana, Phaseolus coccineus, Phaseolus limensis, Phaseolus vulgaris, Phytolacca americana, Pisum sativum, Pseudomonas aeruginosa, Psophocarpus tetragonolobus, Ptilota plumosa, Ricinus communis, Robinia pseudoacacia, Sambucus nigra, Solanum tuberosum, Sophora japonica, Tetragonolobus purpureas, Triticum vulgaris, Ulex europaeus, Vicia faba, Vicia sativa, Vicia villosa, Vigna radiata, Viscum album*, and *Wisteria floribunda*. Lectins are proteins produced by plants and some animal species that bind specifically and non-covalently to sugar groups that are present on the surface of blood cells.

Preferably, the lectin is capable of binding both erythrocytes and leukocytes and is not blood-cell-group specific. Many other examples of lectins are known and need not be described further here.

The pad of porous material can alternatively be impregnated with a carbohydrate capable of aggregating blood cells, such as the carbohydrates disclosed in U.S. Pat. No. 4,678,757 by Rapkin et al., incorporated herein by this reference. These carbohydrates include, but are not necessarily limited to, mannitol, sorbitol, inositol, β-D-glucose, α-D-glucose, D(+)xylose, D(+)mannose, D(−)arabinose, L(+)arabinose, D(+)galactose, L(−)xylose, D-glucoheptose, L-lyxose, lactose, maltose, and sucrose. A particularly preferred carbohydrate is mannitol. Although applicants do not intend to be bound by this theory, these carbohydrates are believed to act by binding non-covalently to the surface of erythrocytes, making them adhesive and causing them to clump or aggregate.

A carbohydrate in solution is applied to a permeable matrix such as a non-woven fiber (e.g., cellulose, glass, or polyester) in a concentration up to 20% (w/v) to produce a treated matrix. The solution can be applied by various means such as impregnation, printing, or spraying to achieve the desired concentration in the matrix. The carbohydrate functions as a holding, clumping, or agglutinating agent which preferentially separates cells from the surrounding liquid which is free to migrate through the matrix.

The volume of blood separated is a function of the absorbent capacity of the treated matrix, the means, attached to the pad, for facilitating the flow of the liquid portion of the blood through interstices around the trapped cellular components of the blood and from the pad, and the degree and area of adherence between the treated matrix and the means for facilitating the flow of the liquid portion of blood.

B. Particular Embodiments of Devices for On-Board Processing

One embodiment of a device for on-board processing according to the present invention comprises:

(1) a first porous separating matrix permeable to the liquid portion of blood but capable of trapping the cellular components of blood; and (2) a second porous matrix in operable contact with the first porous separating matrix that permits the liquid portion of the blood to flow by capillary action or chromatographic separation through the second porous matrix without significant hemolysis.

In this embodiment, the second porous matrix comprises the means, attached to the pad, for facilitating the flow of the liquid portion of the blood through interstices around the trapped cellular components of the blood and from the pad of porous material. The second porous matrix can be a membrane such as a membrane suitable for chromatographic separation. Typical materials for such membranes include, but are not limited to, nitrocellulose, cellulose, other cellulose derivatives, nylon, rayon, paper, silica, polyesters, and polysulfones. A generally preferred material for such membranes is nitrocellulose. The chromatographic medium can be pretreated or modified as needed.

This second porous matrix can have capture zones thereon for binding members of a specific binding pair, such as antigens, haptens, or antibodies. For example, the second porous matrix can have, immobilized in the capture zone, a first antibody for binding analyte, which is then detected by means of a labeled second antibody in a sandwich reaction. Alternatively, the second porous matrix can have an antigen immobilized in the capture zone for binding of an antibody. More than one capture zone can be present on the same second porous matrix; if more than one capture zone is present, they can have the same or different members of a specific binding pair bound thereto. If more than one capture zone is present, one capture zone can be used as a control to ensure that the assay has been performed properly. Many arrangements are well known in the art and need not be recited further. The second porous matrix can therefore comprise a chromatographic assay element, which can be used for the performance of an immunochromatographic assay. When the second porous matrix is a chromatographic assay element, the device is capable of performing on-board separation of the cellular components of the blood from the liquid portion of the blood and an assay for an analyte in the liquid portion of the blood in a unitary device. The assay can be carried out by applying the blood sample to the first separating matrix and subsequently reading the result.

Typically, the chromatographic assay element performs either a competitive immunoassay or a sandwich immunoassay, as these formats are generally known in the art. For a sandwich immunoassay, the labeled component found in the chromatographic medium is typically a labeled specific binding partner specific for the analyte. Several different arrangements are possible. If the analyte is an. antigen, the chromatographic medium can include in the capture zone an immobilized unlabeled first antibody to the analyte, and the labeled antibody can then be a second antibody to the analyte If the first and second antibodies bind to the identical epitope, the antigen should have multiple antibody-binding sites so that two or more antibodies can be bound to the same antigen molecule to form the sandwich. Alternatively, the first and second antibodies can bind to different epitopes. Polyclonal or monoclonal antibodies or mixtures can be used. The immobilization of antibodies and other specific binding partners to test strips is well known in the art and need not be described in detail here. However, such immobilization can either be by way of covalent or non-covalent interactions, depending on the chromatographic medium used and the nature of the immobilized specific binding partner.

The labeled component bound to the chromatographic medium, in the case of a sandwich immunoassay, is typically a labeled antibody to the analyte. If the analyte is itself an antibody, such as in the case of an assay for the detection of antibody in human serum to the bacterium Helicobacter pylori, suspected of being the causative agent of stomach ulcers, the labeled component can be a second antibody that binds the first antibody on the basis of species, class, or subclass specificity. Class specificity is also known as isotype specificity, such as IgG, IgM, IgA, IgD, and IgE for human antibodies. Subclass specificity refers to antigenic differences within classes, such as IgG1, IgG2, IgG3, and IgG4, which are subclasses of IgG. It is highly preferred that the labeled specific binding partner used for detection of an antibody analyte binds to the constant region of the antibody analyte, in order to prevent interference.

In some applications, it is desirable to employ indirect labeling. For example, in testing for Giardia antigen, an IgM antibody can be used that may be difficult to label directly. In that case, a secondary specific binding partner specific for the mobile first specific binding partner can be labeled. Typically, the labeled secondary specific binding partner binds to the antibody that is the first specific binding partner on the basis of species, class, or subclass specificity. The first specific binding partner has specific binding affinity for the analyte. As an alternative to the use of a secondary specific binding partner, the first specific binding partner can be conjugated to biotin and an avidin-conjugated label can be used.

When a competitive immunoassay is performed, the label is typically an analyte or analyte analog. However, other labeling schemes are known in the art; in some of these labeling schemes, the label is a labeled antibody to the analyte or a secondary specific binding partner. In some cases, anti-idiotypic antibodies can be used for competitive immunoassays.

An additional element or elements can be interposed between the first porous separating matrix and the second porous matrix. These elements, which are typically conducting, can act as a bridge between the first porous separating matrix and the second porous matrix, i.e, the chromatographic assay element.

Optionally, and preferably, the second porous matrix is fixedly attached to a solid support that is impermeable. The second porous matrix can be laminated to the support or cast onto it. The solid support can be made of materials such as plastic or laminated cardboard.

Such a device is shown in FIG. 1. The device includes a first porous separating matrix 12, a second porous matrix 14 in operable contact with the first porous separating matrix 12, and a solid support 16. The first porous separating matrix 12 has a first surface 18 and a second surface 20. The second porous matrix 14 can be a chromatographic assay element.

In use, a blood sample 22 is added to the first surface 18 of the first porous separating matrix 12, and the liquid portion of the blood sample 22 migrates into the second porous matrix 14 as a result of the contact between the second surface 20 of the first porous separating matrix 12 and the second porous matrix 14 after the cellular elements are trapped within the first porous separating matrix 12. A chromatographic assay can be performed within the second porous matrix 14.

Figure 2:
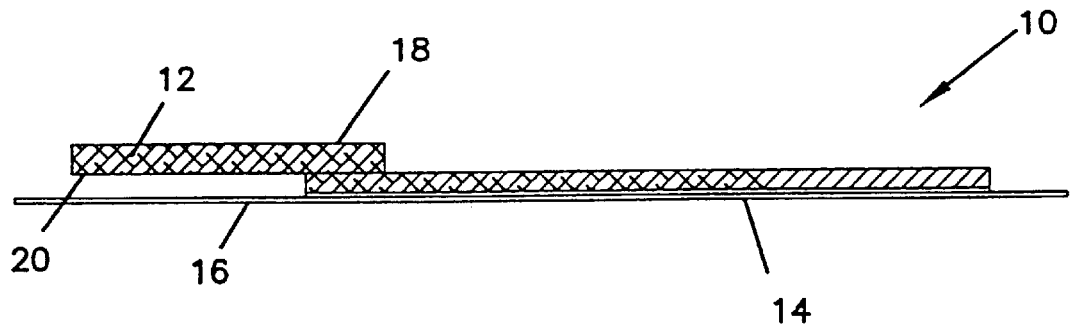
FIG. 2 is another drawing of the device shown in FIG. 1, showing the migration of blood through the device.

FIG. 2 shows the device of FIG. 1 after the liquid portion of the blood sample has migrated into the second porous matrix 14. The cross-hatched regions in FIG. 2 represent the areas of liquid flow through the first porous matrix 12 and the second porous matrix 14.

In an alternative version of this embodiment, the first separating matrix can be an untreated asymmetric membrane. The untreated asymmetric membrane is constructed in such a way that it has a decreasing gradient of pore size within the membrane. The asymmetric membrane has a first surface and a second surface; the blood sample is applied to the first surface. The pore size decreases from the first surface to the second surface. The asymmetric membrane is capable of trapping the cellular components of blood within it and allowing the liquid components of blood to pass through. The first separating matrix permits the liquid portion of the blood to flow through on contact with the second matrix, as described above.

This device is also depicted by the drawings of FIGS. 1 and 2, with the first surface 18 and second surface 20 of the asymmetric membrane as the first porous separation matrix 12. Blood flow is from the first surface 18 to the second surface 20 of the asymmetric membrane.

Asymmetric membranes suitable for use in on-board separating devices according to the present invention can be prepared from combinations of hydrophobic and hydrophilic polymers, such as disclosed in U.S. Pat. No. 5,240,862 to Koenhen et al. and U.S. Pat. No. 5,076,925 to Roesink et al. The hydrophobic polymer can be polysulfone, polyether sulfone, polyimide, or polyetherimide, and the hydrophilic polymer can be polyvinyl pyrrolidone, polyacrylic acid, polyvinyl alcohol, polyvinyl acetate, or polyethylene glycol.

In yet another alternative version of this embodiment, the first matrix can be constructed in such a way that only a portion of the pad is capable of binding the cellular components of blood. In other words, the pad can be divided into two sectors, a first sector that permits flow but is not capable of binding the cellular components of blood and a second sector that is capable of binding the cellular components of blood. The second sector can contain antibodies, lectins, or carbohydrates as described above. The first sector typically contains reagents for pretreatment of the blood sample that can be premixed into the blood sample when the blood migrates through the first sector.

Figure 3:
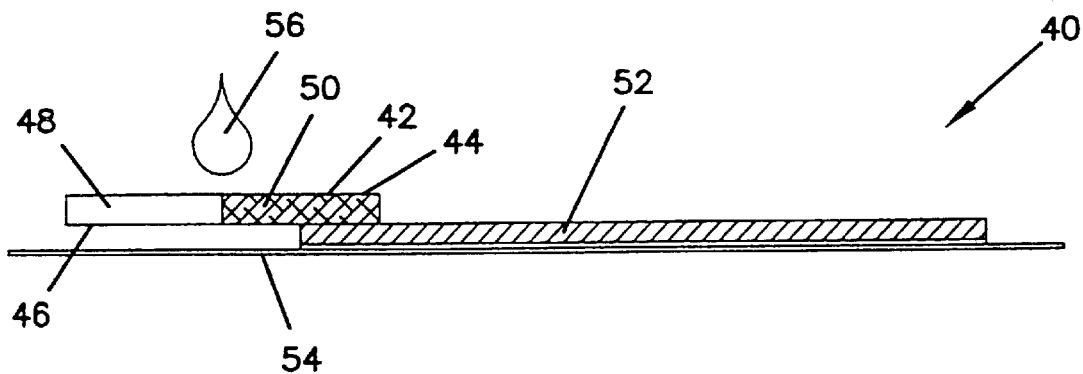
FIG. 3 is a drawing of another embodiment of an assay device according to the present invention employing a porous pad with two sectors.

This alternative version of the device is depicted in FIG. 3. The device 40 has a first separating matrix 42 with a first surface 44 and a second surface 46, with two sectors, a first sector 48 that is not capable of binding the cellular components of blood and a second sector 50 that is capable of binding the cellular components of blood. The device also has a second porous matrix 52 and a solid support 54.

In use, a blood sample 56 is added to the first surface 44 of the first separating matrix 42, and it migrates from the first sector 48 to the second sector 50, typically premixing the reagents present in the first sector 48 into the blood sample 56 for pretreatment of the blood sample 56. The liquid portion of the blood sample 56 then migrates to the second porous matrix 52 from the second sector 50; a chromatographic assay can be performed in the second porous matrix 52.

In still another alternative version of this embodiment, three elements are used:

(1) a first porous separating matrix permeable to the liquid portion of blood but capable of trapping the cellular components of blood;

(2) a second porous separating matrix in operable contact with the first porous separating matrix permeable to the liquid portion of blood but capable of trapping the cellular components of blood; and (3) a third porous matrix in operable contact with the second porous separating matrix that permits the liquid portion of the blood to flow by capillary action or chromatographic separation through the second porous matrix.

The separation of the liquid portion of the blood from the cellular components of the blood occurs by flow through the first and second porous separating matrices without significant hemolysis.

In this alternative version, the third matrix comprises the means for facilitating the flow of the liquid portion of the blood: (i) through interstices around the trapped cellular components of the blood and (ii) from the second matrix. The third matrix can include a chromatographic assay element.

Optionally, and preferably, the third matrix is fixedly attached to a solid support that is impermeable, as described above.

The first and second matrices can be alike or different; they can comprise any of the alternatives described above in Section I(B), including matrices containing a binder for the cellular components of blood such as a lectin or an anti-blood cell antibody, matrices containing a carbohydrate capable of aggregating blood cells, and matrices containing an asymmetric membrane to trap blood cells. Matrices with two sectors can be used.

For this alternative of the device, a method for separating the liquid portion of blood from the cellular components of blood can comprise the steps of:

(1) applying a sample of blood to the first porous separating matrix of the device;

(2) allowing the blood sample to flow through the first porous separating matrix and the second porous separating matrix to separate the liquid portion of the blood sample from the cellular components of the blood sample; and (3) facilitating the flow of the liquid portion of the blood through the interstices around the trapped cellular components of the blood as a result of the action of the third matrix.

When the third matrix includes a membrane for chromatographic separation with a capture zone, a method for performing an assay for detecting and/or determining at least one analyte in the liquid portion of a blood sample can comprise the steps of:

(1) applying a sample of blood to the first porous separating matrix of the device;

(2) allowing the blood sample to flow through the first and second porous separating matrices to separate the liquid portion of the blood sample from the cellular components of the blood sample;

(3) facilitating the flow of the liquid portion of the blood through the interstices around the trapped cellular components of the blood as a result of the action of the third matrix and;

(4) allowing the liquid portion of the blood to flow through the third matrix so that an assay is performed in the second matrix, the assay being performed by binding a member of a specific binding pair to the capture zone of the third matrix to detect and/or determine the at least one analyte.

Figure 4:
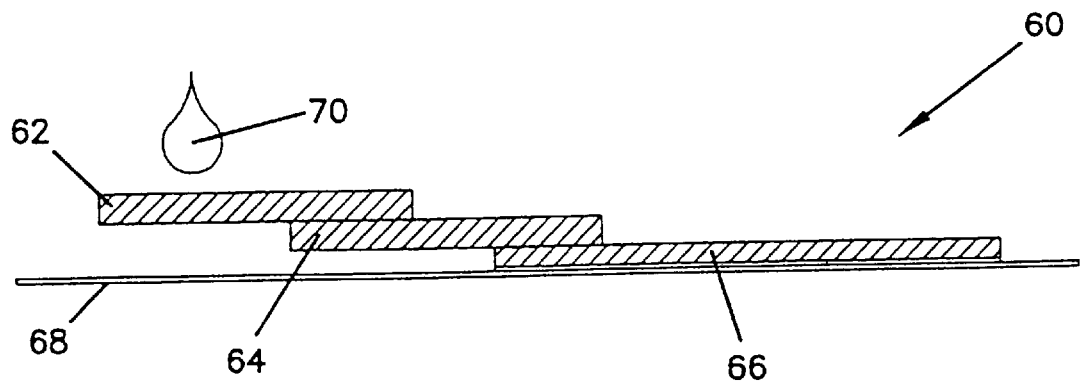
FIG. 4 is a drawing of another embodiment of a device for separating the liquid portion of blood from the cellular components of blood, employing three matrices.

This alternative version of the device is shown in FIG. 4. The device 60 has a first matrix 62, a second matrix 64, a third matrix 66, and a solid support 68. A blood sample 70, applied to the first matrix 62, flows through the first matrix 62 and the second matrix 64; the liquid portion of the blood sample then migrates into the third matrix 66. A chromatographic assay can be performed in the third matrix 66.

In yet another alternative version of this embodiment, the device can include multiple second porous matrices, each second porous matrix being in operable contact with the first porous separating matrix. Each second porous matrix can comprise a chromatographic assay element, with a capture zone, as described above. When the second porous matrices include chromatographic assay elements with capture zones, a method for performing an assay for detecting and/or determining at least one analyte in the liquid portion of a blood sample can comprise the steps of:

(1) applying a sample of blood to the first porous separating matrix of the device;

(2) allowing the blood sample to flow through the first porous separating matrix to separate the liquid portion of the blood sample from the cellular components of the blood sample;

(3) facilitating the flow of the liquid portion of the blood through the interstices around the trapped cellular components of the blood as a result of the action of the second matrices; and (4) allowing the liquid portion of the blood to flow through the second matrices so that an assay is performed in at least one of the second matrices, the assay being performed by binding a member of a specific binding pair to the capture zone of at least one of the second matrices to detect and/or determine the at least one analyte.

Figure 5:
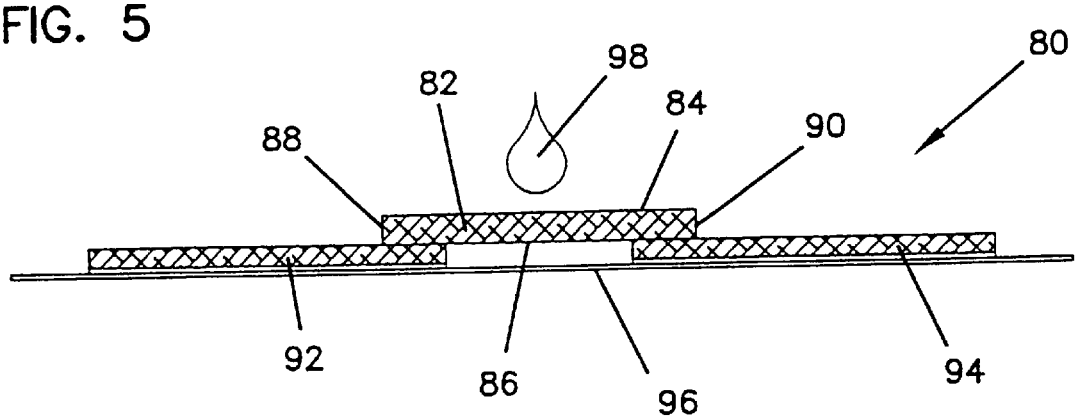
FIG. 5 is a drawing of yet another embodiment of an assay device according to the present invention with two second matrices, which can incorporate assay elements.

In one arrangement, depicted in FIG. 5, the device includes two second porous matrices, one in operable contact with each end of the first porous matrix. In this arrangement, the blood is applied near the center of the first porous matrix, and migrates outward to the ends. Alternatively, three or more second porous matrices can be used, each in operable contact with the first porous matrix. The second porous matrices can be arranged circumferentially around the first porous matrix, like the spokes of a wheel. In this alternative, the first porous matrix can be any of the first porous matrices described above, including the untreated asymmetric membrane.

In FIG. 5, the device 80 comprises a first porous separation matrix 82, with a first surface 84 and a second surface 86 and first and second ends 88 and 90, and two second matrices 92 and 94, as well as a solid support 96. The two second matrices 92 and 94 are in contact with the ends 88 and 90 of the first porous separation matrix 82. A blood sample 98 is added to the first surface 84 of the first porous separation matrix 82 and migrates through the first porous separation matrix 82, with the liquid portions of the blood sample migrating into the two second matrices 92 and 94.

C. Two-Component Assay Devices

Another embodiment of the present invention is a two-component device incorporating the first and second matrices. Such a device, in general, comprises:

(1) a first opposable component including:
   (a) a first porous separating matrix as described above; and
   (b) a second porous matrix in operable contact with the first porous separating matrix as described above; and (2) a second opposable component attachable to the first opposable component such that the first and second opposable components can be brought into opposition to transfer fluid from one of the opposable components to the other by pressure.

A large number of embodiments exist using two opposable components. Several alternatives are depicted below in FIGS. 6 and 7. These alternatives are exemplary and not exclusive; a large number of forms of the assay device exist, and have been described, for example in copending U.S. patent application Ser. No. 08/040,430 incorporated herein by this reference.

For example, the second opposable component can include a sample preparation zone, which can then include at least one reagent for treatment of the sample. This reagent can be used for treatment of the sample before the separation of the liquid portion of the blood from the cellular components of the blood.

Alternatively, the sample preparation zone can include a specific binding partner labeled with a detectable label. The specific binding partner can have specific binding affinity for at least one component selected from the analyte and a specific binding partner for the analyte in a form that can be resolubilized by the addition of an aqueous sample to the sample preparation zone. In other words, the labeled specific binding partner can be applied to the sample preparation zone in liquid form and dried down in such a way that it will be redissolved. Typically, when the device is used for a sandwich immunoassay, the specific binding partner labeled with the detectable label has specific binding affinity for the analyte.

Alternatively, the first opposable component can further include a sample preparation zone, which can include a specific binding partner labeled with a detectable label in resolubilizable form. As indicated below, in this case, the sample preparation zone on the first opposable component would be contacted by an element on the second opposable component when the first and second opposable components are brought into opposition. This will result in the transfer of the sample; the sample and the resolubilized labeled specific binding partner are then applied to the porous pad.

Alternatively, in a two-component device, the porous pad can be on the opposite component from the chromatographic medium. An example of this arrangement is shown below in FIG. 6.

A method for performing an assay for detecting and/or determining at least one analyte in the liquid portion of a blood sample can comprise the steps of:

(1) applying a sample of blood to the first porous separating matrix on the first opposable component of the two-component assay device;

(2) allowing the blood sample to flow through the first porous separating matrix to separate the liquid portion of the blood sample from the cellular components of the blood sample;

(3) facilitating the flow of the liquid portion of the blood through the interstices around the trapped cellular components of the blood as a result of the action of the second matrix;

(4) bringing the first and second opposable components into opposition to transfer fluid from one of the opposable components to the other by pressure; and (5) allowing the liquid portion of the blood to flow through the second matrix so that an assay is performed in the second matrix, the assay being performed by binding a member of a specific binding pair to the capture zone of the second matrix to detect and/or determine the at least one analyte.

Several examples of two-component assay devices are shown.

Figure 6:
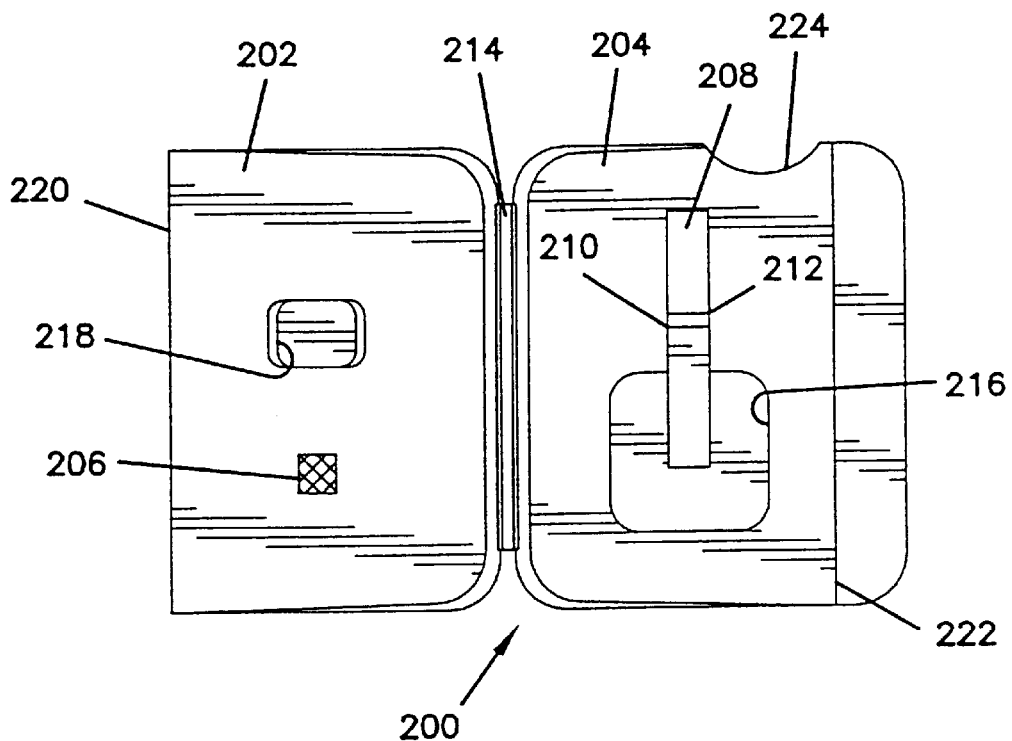
FIG. 6 is a drawing of an embodiment of a two-component device according to the present invention.

One general arrangement is shown in FIG. 6. The assay device 200 has a first opposable component 202 and a second opposable component 204. The first opposable component 202 includes a porous pad 206 for application of the sample. The second opposable component 204 contains a chromatographic medium 208. The means for withdrawing a liquid portion of blood from the porous material is formed by the overlap between the porous pad 206 and the chromatographic medium 208 when the first and second opposable components 202 and 204 are brought into opposition. The chromatographic medium 208 can include a detection zone 210 and a control zone 212. The first opposable component 202 and the second opposable component 204 are joined by a hinge 214. The chromatographic medium 208 is supported in a well 216. The first opposable component 202 can include a window 218 for viewing of the chromatographic medium 208, including the area of the detection zone 210 and the control zone 212. The first and second opposable components 202 and 204 can be held together by engagers, such as those formed by a beveled edge 220 on the first opposable component 202 and an undercut edge 222 on the second opposable component 204. Other types of engagers can also be used. The device can be accessed through a notch 224 formed in the second opposable component 204.

Figure 7:
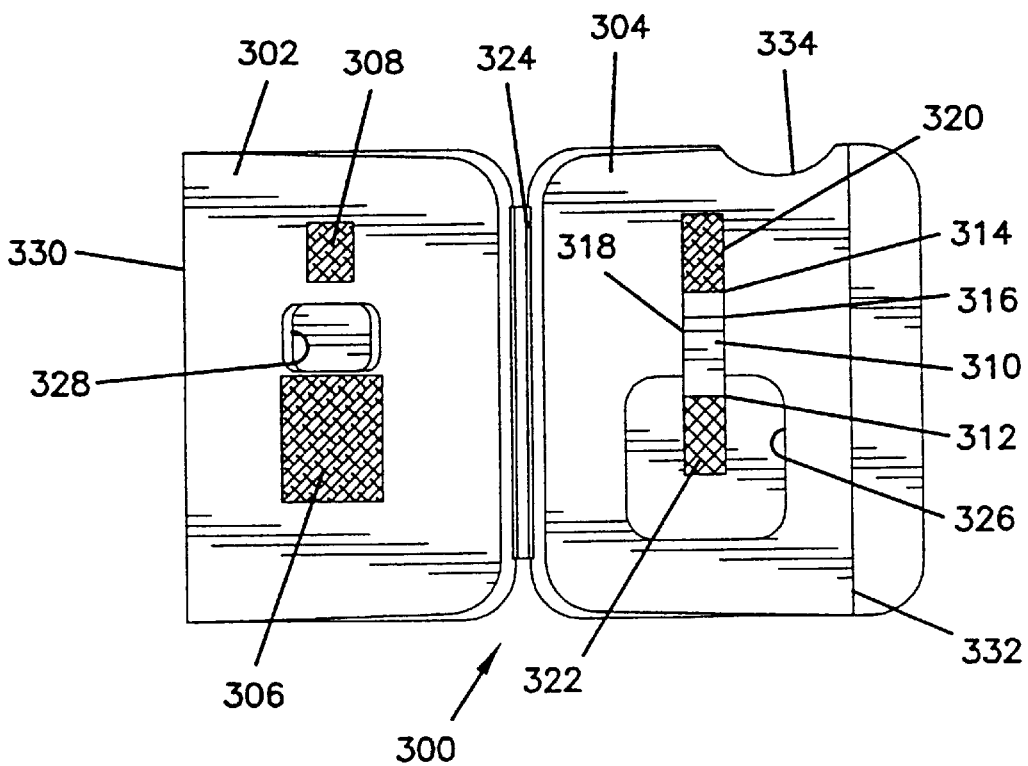
FIG. 7 is a drawing of another embodiment of a two-component device according to the present invention.

Another embodiment of an assay device according to the present invention comprises a device capable of carrying out bidirectional chromatography. This embodiment is shown in FIG. 7. The assay device 300 has a first opposable component 302 and a second opposable component 304. The first opposable component 302 includes an absorber 306, which can be an absorbent pad, and an applicator 308. The second opposable component 304 has a chromatographic medium 310 having a first end 312 and a second end 314, with a detection zone 316 and a control zone 318. The second opposable component 304 also has a conductor 320 in operable contact with the second end 314 of the chromatographic medium 310; the conductor 320 is used for application of a reagent in the applicator 308 to the chromatographic medium 310 when the first and second opposable components 302 and 304 are brought into opposition. The second opposable component 304 also has a pad of porous material 322 permeable to the liquid portion of blood but capable of binding the cellular components of blood as described above. The pad of porous material 322 is in operable contact with the first end 312 of the chromatographic medium 310; this operable contact forms the means for withdrawing the liquid portion of blood from the pad of porous material 322. The first and second opposable components 302 and 304 are joined by a hinge 324. The chromatographic medium 310 and pad of porous material 322 are supported in a well 326. The first opposable component 302 can include a window 328 for viewing of the chromatographic medium 310, including the area of the detection zone 316 and the control zone 318. The first and second opposable components 302 and 304 can be held together by engagers, such as those formed by a beveled edge 330 on the first opposable component 302 and an undercut edge 332 on the second opposable component 304. Other types of engagers can also be used. The device can be accessed through a notch 334 formed in the second opposable component 304.

In use, a blood sample is applied to the porous pad 322 for separating the cellular components of blood. The liquid portion of the blood sample then migrates through the chromatographic medium 310; at that point, the first and second opposable components 302 and 304 are brought into opposition, and a reagent in the applicator 308 is applied to the chromatographic medium 310 and migrates through the chromatographic medium 310 in the opposite direction from the flow of the liquid portion of the blood sample through the chromatographic medium 310, thus reversing the flow. The reversal of flow is driven by the absorber 306.

This embodiment is particularly suitable for the performance of serological assays to detect antibodies in blood samples. For example, if the analyte to be detected is human antibody to the bacterium *Helicobacter pylori*, believed to be the cause of stomach ulcers, a blood sample suspected of containing the antibody can be applied to the porous pad 322 to separate the cellular components of the blood sample from the liquid portion of the blood sample. The liquid portion of the blood sample then migrates from the porous pad 322 to the chromatographic medium 310. The detection zone 316 can contain immobilized *H. pylori* antigen, so that any antibody specific for *H. pylori* antigen binds at the detection zone. The applicator 308 then contains a labeled antibody that binds human immunoglobulin G antibody, such as a gold-labeled goat anti-human immunoglobulin G antibody, in resolubilizable form. The contents of the applicator 308 are resolubilized by the addition of an aqueous liquid to the applicator 308. When the first and second opposable components 302 and 304 are brought into opposition, the applicator 308 is brought into contact with the chromatographic medium 310 to apply the labeled anti-human IgG antibody to the chromatographic medium 310. The absorber 306 then causes the labeled anti-human IgG antibody to migrate through the chromatographic medium 310 in a direction opposite to the flow of the liquid portion of the blood sample through the chromatographic medium 310. Any anti-*H. pylori* antibody bound at the detection zone 316 then becomes labeled. If gold-labeled antibody is used, the presence of anti-*H. pylori* antibody can be detected visually. The reverse flow, driven by the absorber 306, acts as a wash to remove other antibody present in the sample that is not specific for *H. pylori* antigen and is not bound at the detection zone 316 but would otherwise react with the labeled anti-human IgG antibody and give a background. The use of bidirectional flow therefore reduces the background and increases the sensitivity and reliability of the test.

These arrangements are exemplary and are not exhaustive; other arrangements of both unidirectional and bidirectional assay devices according to the present invention incorporating the porous pad for binding the cellular components of blood are also within the scope of the present invention. These arrangements can include a number of elements.

For example, in a number of devices according to the present invention, absorbers are in operable contact with one end of the chromatographic medium, typically the end opposite from the end with which contact is made with the pad of porous material. The absorbers can be made of any bibulous material that will hold a liquid sufficiently so liquid can be drawn through the chromatographic medium and accumulated in the absorber. Typical materials for the absorbers include, but are not limited to, filter paper.

Additionally, the devices can include one or more conductors. Conductors can serve as a bridge between the pad of porous material and the chromatographic medium wherefore constituting the means for withdrawing the liquid portion of blood from the porous material. These conductors are prepared of hydrophilic media that pass liquids without substantially absorbing them. Such materials are well-known in the art. Cellulose and cellulose derivatives can be used.

In devices according to the present invention that employ opposable components, the bodies of the opposable components are preferably made of laminated cardboard that is sufficiently impervious to moisture to contain the liquids involved in the performance of the assay carried out by the device. Other cellulose-based materials, such as paperboard or solid bleached sulfite (SBS) can also be used. Alternatively, the bodies of the opposable components can be made of plastic that is impervious to moisture. A suitable plastic is a polycarbonate plastic such as Lexan™.

The opposable components are joined by a hinge, preferably made of a material impermeable to liquids, such as a plastic that can be compatibly joined with or is the same as a material used for the first and second opposable components.

A version particularly adapted for the performance of bidirectional assays can comprise:

(1) a first opposable component including:
   (a) a first porous separating matrix permeable to the liquid portion of blood but capable of trapping the cellular components of blood; and
   (b) a second porous matrix including a membrane for chromatographic separation in operable contact with the first porous separating matrix that permits the liquid portion of the blood to flow in a first direction by capillary action or chromatographic separation through the second porous matrix; and (2) a second opposable component attachable to the first opposable component such that the first and second opposable components can be brought into opposition to transfer a reagent from the second opposable component to the first opposable component by pressure so bringing the first and second opposable components into opposition causes the reagent transferred from the second opposable component to the first opposable component to migrate through the second porous matrix in a second direction opposite to the first direction.

Typically, in this version, the membrane for chromatographic separation includes therein a capture zone for binding an analyte and the reagent transferred from the second opposable component to the first opposable component is a labeled specific binding partner for the analyte.

A method for performing an assay for detecting and/or determining at least one analyte in the liquid portion of a blood sample using this version can comprise the steps of:

(1) applying a sample of blood to the first porous separating matrix on the first opposable component of the device;

(2) allowing the blood sample to flow through the first porous separating matrix to separate the liquid portion of the blood sample from the cellular components of the blood sample;

(3) allowing the liquid portion of the blood sample to flow through the membrane for chromatographic separation in the first direction;

(4) bringing the first and second opposable components into opposition to transfer the labeled specific binding partner for the analyte from the second opposable component to the first opposable component by pressure; and (5) allowing the labeled specific binding partner for the analyte to flow through the membrane for chromatographic separation in the second direction so that an assay is performed in the second matrix, the assay being performed by binding the labeled specific binding partner to the capture zone of the second matrix to detect and/or determine the at least one analyte.

The description of the devices above is directed to assay devices that perform one assay at a time. However, assay devices according to the present invention can also be constructed that can perform multiple assays at the same time. The assays can be performed for the same analyte or different analytes. This allows the application of multiple blood samples to a single device with the performance of multiple assays.

II. DEVICES AND METHODS FOR OFF-BOARD PROCESSING

Another aspect of the present invention is a method for separating the liquid portion of blood from the cellular components of blood by the pre-addition of a binder for the cellular components of blood to a sample of whole blood before the mixture is applied to a device for separating the liquid portion of blood from the cellular components of blood.

One such method comprises:

(1) adding a cross-linking substance for the cellular components of blood to a sample of whole blood, the cross-linking substance being selected from the group consisting of a lectin, an anti-blood cell antibody, and a carbohydrate capable of aggregating blood cells;

(2) mixing the cross-linking substance and the blood sample to form a mixture of the cross-linking substance and the blood sample, or allowing time for mixing to occur;

(3) applying the mixture of the cross-linking substance and the blood sample to a device for separating the liquid portion of blood from the cellular components of blood, the device comprising:

(a) a pad of porous material permeable to the liquid portion of blood but capable of trapping the cellular components of blood aggregated by the reaction between the cross-linking substance and the blood sample;

(b) a substrate supporting the pad; and (c) means, attached to the pad, for facilitating the flow of the liquid portion of the blood: (i) through interstices around the trapped cellular components of the blood and (ii) from the pad of porous material; and (4) allowing the liquid portion of the blood to flow through the pad to separate the liquid portion of the blood from the cellular components of the blood.

The separation of the liquid portion of blood from the cellular components of the blood bound to the binder occurs by flow through the pad without significant hemolysis. This method differs from the methods described above in that the pad of porous material need not contain a cross-linking substance such as an antibody or a lectin; rather the pad acts as a filter to remove cellular components of blood aggregated by previous binding to the cross-linking substance, with the binding occurring before the sample is applied to the pad.

Preferably, an anticoagulant is added with the cross-linking substance. A typical anticoagulant is EDTA or heparin, although other anticoagulants are known in the art.

Preferably, a concentration of cross-linking substance is used that is sufficient to cross-link substantially all cellular elements of blood.

The device for separating the liquid portion of blood from the cellular components of blood can be any of the alternatives described above in Section I, with the difference that the pad of porous material acts as a filter for removing already agglutinated or aggregated cellular components of blood instead of providing means for agglutination or aggregation of the cellular components.

The separated liquid portion of the blood can then be assayed for an analyte as described above, typically by an immunochromatographic procedure. If the device used for separating the liquid portions of blood from the cellular components of blood includes a chromatographic medium, as described above, the assay can be performed in the device; this is generally preferred. Otherwise, the separated liquid portion of the blood can be drawn off for an assay on another device. These assays can be performed on assay devices such as those disclosed in copending U.S. patent application Ser. No. 08/040,430 by Howard M. Chandler et al., entitled "Opposable-Element Chromatographic Assay Device," incorporated herein by reference. These devices include both unidirectional and bidirectional assay devices.

Alternatively, instead of adding the cross-linking substance to a sample of whole blood, a sample of blood can be added to a capillary tube coated with a cross-linking substance, with or without an anticoagulant. The cross-linking substance and anticoagulant, if present, are then allowed to dissolve in the blood sample. The blood sample with the cross-linking substance and anticoagulant dissolved therein is then applied to the device for separating the liquid portion of blood from the cellular components of blood as described above. Again, the device acts as a filter for the agglutinated or aggregated blood cells. An assay can be performed as described above.

Figure 8:
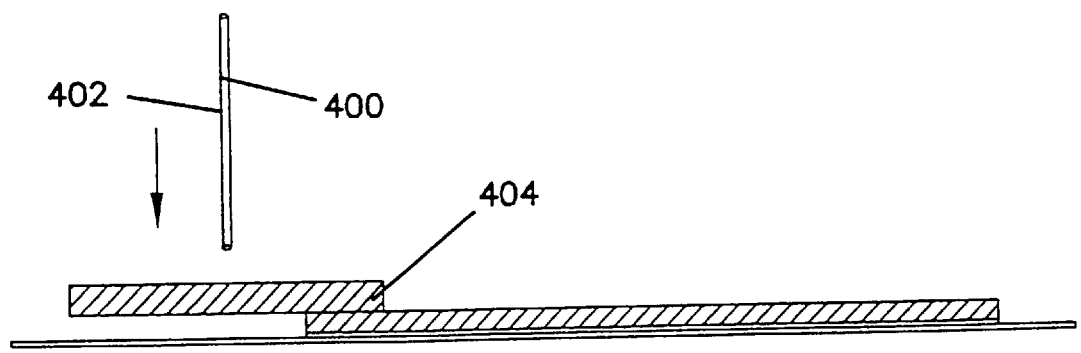
FIG. 8 is a schematic diagram of a method according to the present invention for separating the liquid portion of blood from the cellular components of blood, employing off-board separation, with blood being added to a capillary tube containing a cross-linking substance for the cellular components of blood.

This alternative is shown generally in FIG. 8. The blood sample 400 is added to the capillary tube 402 and, after mixing, the capillary tube is applied to the separation device 404.

ADVANTAGES OF THE INVENTION

The present invention provides a rapid, efficient, and simple means of separating blood cells from the liquid portion of blood for the performance of specific binding assay such as immunoassays as well as other tests. In particular, the present invention provides an integrated device that incorporates both an assay element and means for separating the liquid portions of blood from the cellular components of blood so that an analyte present in the liquid portions of blood can be assayed readily. This avoids the necessity of a preliminary extraction of serum or plasma from blood with the intended necessity of safe disposal of the blood fractions. The use of an assay device according to the present invention allows for convenient and safe disposal of used test devices. Additionally, the improved device is capable of direct assay of a desired analyte when a whole blood sample is applied to the device.

Assay devices according to the present invention can perform a broad range of immunoassays, including both sandwich and competitive immunoassays. In particular, assay devices according to the present invention are suitable for the detection and/or determination of both antigens and antibodies.

Although the present invention has been described with considerable detail, with reference to certain preferred variations thereof, other versions and embodiments are possible. These versions include other arrangements of two-component devices that operate by the basic principles described herein. These versions include assay devices adapted for competitive immunoassays as well as sandwich immunoassays in various arrangements. In particular, devices according to the present invention can be adapted to make use of radial or circumferential flow through a chromatographic medium rather than linear flow. Devices according to the present invention can also be adapted to perform multiple assays simultaneously, with multiple second porous matrices, arranged circularly or like the spokes of a wheel, or in other arrangements. Although devices according to the present invention are particularly adapted for the separation of the liquid portion of blood from the cellular components of blood and the performance of assays on the liquid portion of blood, devices according to the present invention can also be used for the removal of blood cells from other body fluids that may contain them, such as cerebrospinal fluid, and for assays on such fluids after the removal of blood cells from them. Devices according to the present invention can also be adapted to perform other assays, such as enzyme assays and colorimetric assays.

The present invention further encompasses variations in which the two components of the device are not held in a permanently fixed arrangement, but can be separated and brought together to perform the assay, such as by electrical or magnetic forces or by using a separable fastener such as a hook-and-eye fabric, for example Velcro™. Additionally, the present invention can also encompass devices having three components in a folding arrangement. Therefore, the scope of the invention is determined by the following claims.

We claim:

1. A device for separating the liquid portion of blood from the cellular components of blood comprising:
   (a) a first opposable component including:
      (i) a first porous separating matrix permeable to the liquid portion of blood but capable of trapping the cellular components of blood; and
      (ii) a second porous matrix in operable contact with the first porous separating matrix that permits the liquid portion of the blood to flow by capillary action through the second porous matrix; and
   (b) a second opposable component attachable to the first opposable component for applying fluid to the first opposable component such that the first and second opposable components can be brought into opposition to transfer fluid from the second opposable component to the first opposable component by pressure;
   whereby the separation of the liquid portion of blood from the cellular components of the blood occurs by flow through the first and second matrices of the first opposable component without significant hemolysis.

2. The device of claim 1 wherein the first porous separating matrix contains a binder for the cellular components of blood.

3. The device of claim 2 wherein the binder is an anti-blood cell antibody.

4. The device of claim 3 wherein the anti-blood cell antibody is an anti-erythrocyte antibody.

5. The device of claim 2 wherein the binder is a lectin.

6. The device of claim 5 wherein the lectin is selected from the group consisting of concanavalin A, abrin, phytohaemagglutinin, limulin, and the lectins produced by the following species: *Agaricus bisporus, Anguilla anguilla, Arachis hypogaea, Bandeiraea simplicifolia, Bauhinia purpurea, Caragana arborescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Lycopersicon esculentum, Maclura pomifera, Momordica charantia, Mycoplasma gallisepticum, Naja mocambique, Naja kaouthia, Perseau americana, Phaseolus coccineus, Phaseolus limensis, Phaseolus vulgaris, Phytolacca americana, Pisum sativum, Pseudomonas aeruginosa, Psophocarpus tetragonolobus, Ptilota plumosa, Ricinus communis, Robinia pseudoacacia, Sambucus nigra, Solanum tuberosum, Sophora japonica, Tetragonolobus purpureas, Triticum vulgaris, Ulex europaeus, Vicia faba, Vicia sativa, Vicia villosa, Vigna radiata, Viscum album,* and *Wisteria floribunda.*

7. The device of claim 1 wherein the first porous separating matrix is impregnated with a carbohydrate capable of aggregating blood cells.

8. The device of claim 7 wherein the carbohydrate is selected from the group consisting of mannitol, sorbitol, inositol, β-D-glucose, α-D-glucose, D(+)xylose, D(+) mannose, D(−)arabinose, L(+)arabinose, D(+)galactose, L(−)xylose, D-glucoheptose, L-lyxose, lactose, maltose, and sucrose.

9. The device of claim 8 wherein the carbohydrate is mannitol.

10. The device of claim 1 wherein the second matrix is a membrane for chromatographic separation.

11. The device of claim 10 wherein the membrane for chromatographic separation has a capture zone thereon for binding a member of a specific binding pair.

12. The device of claim 1 wherein the first porous separating matrix is an asymmetric membrane with a first surface and a second surface, the membrane having a gradient of pore sizes such that the pore size decreases from the first surface to the second surface, the asymmetric membrane capable of trapping the cellular components of blood within it and allowing the liquid components of blood to pass through.

13. The device of claim 1 wherein the first porous separating matrix includes two sectors:
   (i) a first sector permeable to both the liquid portion of blood and the cellular components of blood; and
   (ii) a second sector permeable to the liquid portion of blood but capable of binding the cellular components of blood.

14. The device of claim 1 wherein the second opposable component includes a sample application zone for transferring fluid to the first opposable component, the fluid including a blood sample.

15. The device of claim 14 wherein the sample application zone for transferring fluid from the second opposable component to the first opposable component includes at least one reagent for treatment of the sample.

16. The device of claim 14 wherein the sample application zone on the second opposable component includes a specific binding partner labeled with a detectable label, the specific binding partner having specific binding affinity for at least one component selected from the group consisting of the analyte and a specific binding partner for the analyte in a form that can be resolubilized by the addition of an aqueous sample to the sample application zone on the second opposable component.

17. The device of claim 16 wherein the specific binding partner labeled with the detectable label has specific binding affinity for the analyte.

18. A method for performing an assay for detecting or determining at least one analyte in liquid portion of a blood sample comprising the steps of:
   (a) applying a sample of blood to the sample application zone on the second opposable component of the device of claim 11 to resolubilize a labeled specific binding partner in the sample application zone;
   (b) bringing the first and second opposable components into opposition to transfer fluid from the second opposable component to the first opposable component by pressure, the fluid including the blood sample and the resolubilized labeled specific binding partner;
   (c) allowing the blood sample to flow through the first porous separating matrix to separate the liquid portion of the blood sample from the cellular components of the blood sample;
   (d) facilitating the flow of the liquid portion of blood through the interstices around the trapped cellular components of the blood as a result of the action of the second matrix; and
   (e) allowing the liquid portion of the blood to flow through the second matrix so that an assay is performed in the second matrix, the assay being performed by binding a member of a specific binding pair that captures onto the second matrix to detect or determine the at least one analyte, at least one member of the specific binding pair binding to the analyte.

19. A device for separating the liquid portion of blood from the cellular components of blood comprising:

(a) a first opposable component including a porous pad for application of a blood sample, wherein the porous pad includes a first porous separating matrix permeable to the liquid portion of blood but capable of trapping the cellular components of blood; and (b) a second opposable component attachable to the first opposable component so that the first and second opposable components can be brought into opposition to transfer fluid from the first opposable component to the second opposable component by pressure, the second opposable component for receiving fluid from the first opposable component, the second opposable component including therein a second porous matrix in operable contact with the first porous separating matrix when the first and second opposable components are brought into opposition, the second porous matrix permitting the liquid portion of the blood to flow by capillary action through the second porous matrix; whereby the separation of the liquid portion of the blood from the cellular components of the blood occurs by flow through the first and second matrices without significant hemolysis.

20. The device of claim 19 wherein the first porous separating matrix contains a binder for the cellular components of blood.

21. The device of claim 20 wherein the binder is an anti-blood cell antibody.

22. The device of claim 21 wherein the anti-blood cell antibody is an anti-erythrocyte antibody.

23. The device of claim 20 wherein the binder is a lectin.

24. The device of claim 23 wherein the lectin is selected from the group consisting of concanavalin A, abrin, phytohaemagglutinin, limulin, and the lectins produced by the following species: *Agaricus bisporus, Anguilla anguilla, Arachis hypogaea, Bandeiraea simplicifolia, Bauhinia purpurea, Caragana arborescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Lycopersicon esculentum, Maclura pomifera, Momordica charantia, Mycoplasma gallisepticum, Naja mocambique, Naja kaouthia, Perseau americana, Phaseolus coccineus, Phaseolus limensis, Phaseolus vulgaris, Phytolacca americana, Pisum sativum, Pseudomonas aeruginosa, Psophocarpus tetragonolobus, Ptilota plumosa, Ricinus communis, Robinia pseudoacacia, Sambucus nigra, Solanum tuberosum, Sophora japonica, Tetragonolobus purpureas, Triticum vulgaris, Ulex europaeus, Vicia faba, Vicia saliva, Vicia villosa, Vigna radiata, Viscum album,* and *Wisteria floribunda.*

25. The device of claim 19 wherein the first porous separating matrix is impregnated with a carbohydrate capable of aggregating blood cells.

26. The device of claim 25 wherein the carbohydrate is selected from the group consisting of mannitol, sorbitol, inositol, β-D-glucose, α-D-glucose, D(+)xylose, D(+)mannose, D(−)arabinose, L(+)arabinose, D(+)galactose, L(−)xylose, D-glucoheptose, L-lyxose, lactose, maltose, and sucrose.

27. The device of claim 26 wherein the carbohydrate is mannitol.

28. The device of claim 19 wherein the second matrix is a membrane for chromatographic separation.

29. The device of claim 28 wherein the membrane for chromatographic separation has a capture zone thereon for binding a member of a specific binding pair.

30. The device of claim 19 wherein the first porous separating matrix is an asymmetric membrane with a first surface and a second surface, the membrane having a gradient of pore sizes such that the pore size decreases from the first surface to the second surface.

31. The device of claim 19 wherein the first porous separating matrix includes two sectors:

(i) a first sector permeable to both the liquid of portion of blood and the cellular components of blood; and (ii) a second sector permeable to the liquid portion of blood but capable of binding the cellular components of blood.

32. The device of claim 19 wherein the sample application zone includes at least one reagent for treatment of the sample.

33. The device of claim 19 wherein the sample application zone includes a specific binding partner labeled with a detectable label, the specific binding partner having specific binding affinity for at least one component selected from the analyte and a specific binding partner for the analyte in a form that can be resolubilized by the addition of a blood sample to the sample application zone.

34. The device of claim 33 wherein the specific binding partner labeled with a detectable label has specific binding affinity for the analyte.

35. A method for performing an assay for detecting or determining at least one analyte in the liquid portion of a blood sample comprising the steps of:

(a) applying a sample of blood to the porous pad on the first opposable component of the device of claim 33;

(b) allowing the sample to resolubilize the labeled specific binding partner labeled with a detectable label;

(c) bringing the first and second opposable components into opposition to transfer fluid from the first opposable component to the second opposable component by pressure;

(d) allowing the blood sample to flow through the first porous separating matrix of the porous pad to separate the liquid portion of the blood sample from the cellular components of the blood sample;

(e) facilitating the flow of the liquid portion of the blood through the interstices around the trapped cellular components of the blood as a result of the action of the second matrix in the second opposable component; and (f) allowing the liquid portion of the blood to flow through the second matrix so that an assay is performed in the second matrix, the assay being performed by binding a member of a specific binding pair to the capture zone of the second matrix to detect or determine the at least one analyte, at least one member of the specific binding pair binding to the analyte.

* * * * *